United States Patent
Swayze et al.

(10) Patent No.: US 9,597,081 B2
(45) Date of Patent: Mar. 21, 2017

(54) MOTOR DRIVEN ROTARY INPUT CIRCULAR STAPLER WITH MODULAR END EFFECTOR

(71) Applicant: Ethicon Endo-Surgery, Inc., Cincinnati, OH (US)

(72) Inventors: Jeffrey S. Swayze, Hamilton, OH (US); Chester O. Baxter, III, Loveland, OH (US); Frederick E. Shelton, IV, Hillsboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 924 days.

(21) Appl. No.: 13/716,318

(22) Filed: Dec. 17, 2012

(65) Prior Publication Data

US 2014/0166728 A1    Jun. 19, 2014

(51) Int. Cl.
   *A61B 17/115* (2006.01)
   *A61B 17/00* (2006.01)
   *A61B 17/072* (2006.01)

(52) U.S. Cl.
   CPC . *A61B 17/1155* (2013.01); *A61B 2017/00393* (2013.01); *A61B 2017/00398* (2013.01); *A61B 2017/00473* (2013.01); *A61B 2017/00477* (2013.01); *A61B 2017/07214* (2013.01); *A61B 2017/07271* (2013.01)

(58) Field of Classification Search
   CPC .................................................. A61B 17/1155
   USPC ........... 227/175.1–182.1; 604/104, 513, 509, 604/508, 107
   See application file for complete search history.

(56) References Cited

U.S. PATENT DOCUMENTS 4,606,343 A * 8/1986 Conta .................. A61B 17/115
                                                227/178.1
4,805,823 A   2/1989 Rothfuss
                   (Continued)

FOREIGN PATENT DOCUMENTS

EP        0699418 A1    3/1996
EP        1813211 A2    8/2007
                   (Continued)

OTHER PUBLICATIONS

U.S. Appl. No. 13/688,951, filed Nov. 29, 2012, Shelton, IV et al.
                   (Continued)

*Primary Examiner* — Nathaniel Chukwurah
(74) *Attorney, Agent, or Firm* — Frost Brown Todd LLC

(57) ABSTRACT

A surgical stapling device comprises a handle assembly, a shaft assembly, and a stapling head assembly. The shaft assembly comprises a rotary drive shaft that translates between two longitudinal positions to alternate between a tissue clamping mode and a tissue cutting/stapling mode. The stapling head assembly includes a first set of rotary drive elements that convert rotary motion of the drive shaft into a tissue clamping action when the drive shaft is in a distal position. The stapling head assembly also includes a second set of rotary drive elements that convert rotary motion of the drive shaft into a tissue cutting/stapling action when the drive shaft is in a proximal position. The drive shaft may be driven manually or by a motor. The stapling head assembly may be provided in a cartridge form that is removable from the shaft assembly.

18 Claims, 21 Drawing Sheets

(56) References Cited

U.S. PATENT DOCUMENTS

| | | | |
|---|---|---|---|
| 5,205,459 A | 4/1993 | Brinkerhoff et al. | |
| 5,271,543 A * | 12/1993 | Grant | A61B 17/115 |
| | | | 227/179.1 |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,415,334 A | 5/1995 | Williamson, IV et al. | |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,794,475 B2 | 9/2010 | Hess et al. | |
| 2005/0205640 A1 * | 9/2005 | Milliman | A61B 17/115 |
| | | | 227/176.1 |
| 2008/0245841 A1 * | 10/2008 | Smith | A61B 17/115 |
| | | | 227/175.2 |
| 2010/0102105 A1 * | 4/2010 | Soutorine | A61B 17/072 |
| | | | 227/179.1 |
| 2010/0176181 A1 * | 7/2010 | Hessler | A61B 17/115 |
| | | | 227/175.1 |
| 2012/0239010 A1 * | 9/2012 | Shelton, IV | A61B 17/1155 |
| | | | 606/1 |
| 2012/0292366 A1 * | 11/2012 | Nalagatla | A61B 17/1114 |
| | | | 227/175.1 |

FOREIGN PATENT DOCUMENTS

| | | |
|---|---|---|
| EP | 2000102 A2 | 12/2008 |
| EP | 2044888 A2 | 4/2009 |
| GB | 2016991 | 9/1976 |
| WO | WO 97/47231 | 12/1997 |
| WO | WO 03/000138 | 1/2003 |
| WO | WO 2004/112583 | 12/2004 |

OTHER PUBLICATIONS

U.S. Appl. No. 13/688,992, filed Nov. 29, 2012, Scheib et al.
U.S. Appl. No. 13/693,430, filed Dec. 4, 2012, Scheib et al.
U.S. Appl. No. 13/693,455, filed Dec. 4, 2013, Scheib et al.
U.S. Appl. No. 13/706,827, filed Dec. 6, 2012, Measamer et al.
U.S. Appl. No. 13/716,308, filed Dec. 17, 2012, Swayze et al.
U.S. Appl. No. 13/716,313, filed Dec. 17, 2012, Swayze et al.
U.S. Appl. No. 13/716,323, Dec. 17, 2012, Swayze et al.
International Preliminary Report on Patentability dated Jun. 23, 2015 for Application No. PCT/US2013/075243, 11 pages.
International Search Report dated Jun. 27, 2014 for Application No. PCT/US2013/075243, 9 pages.

* cited by examiner

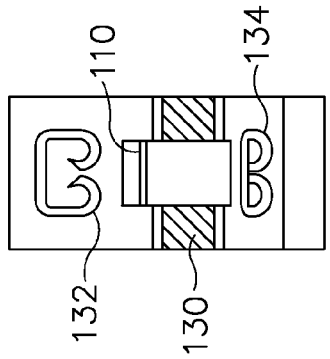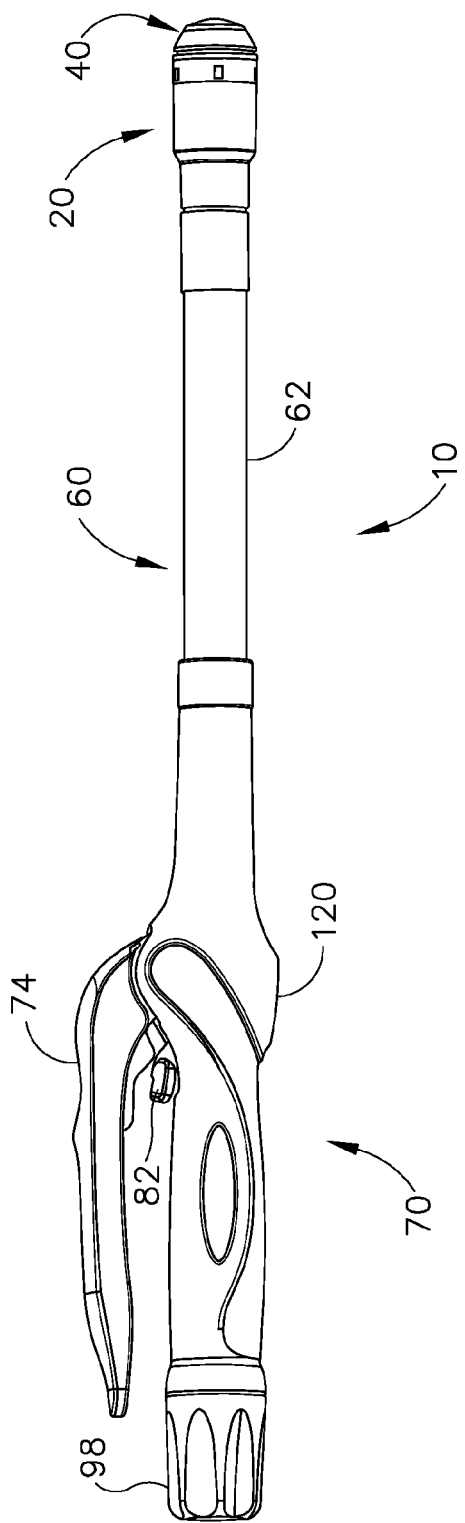

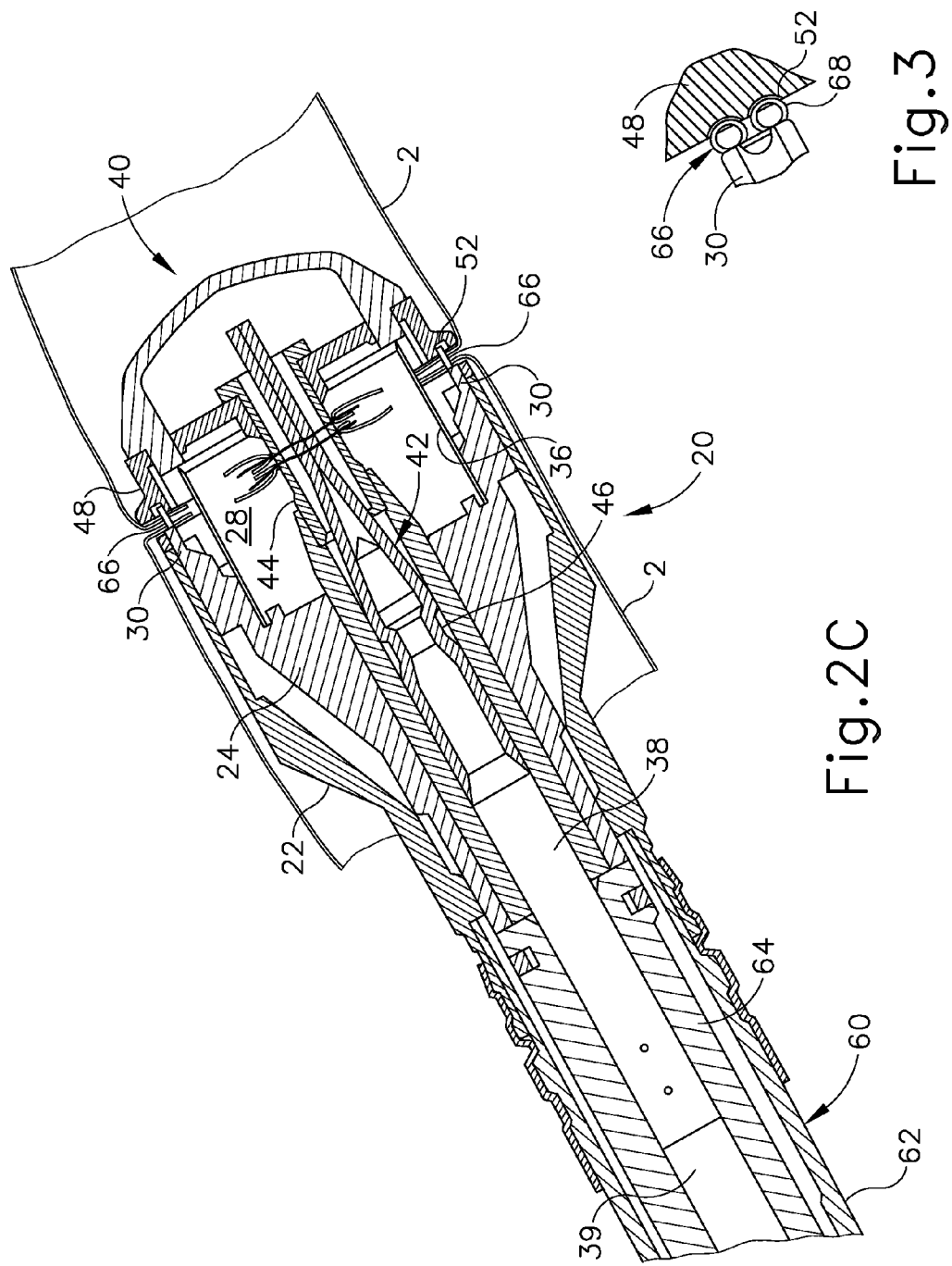

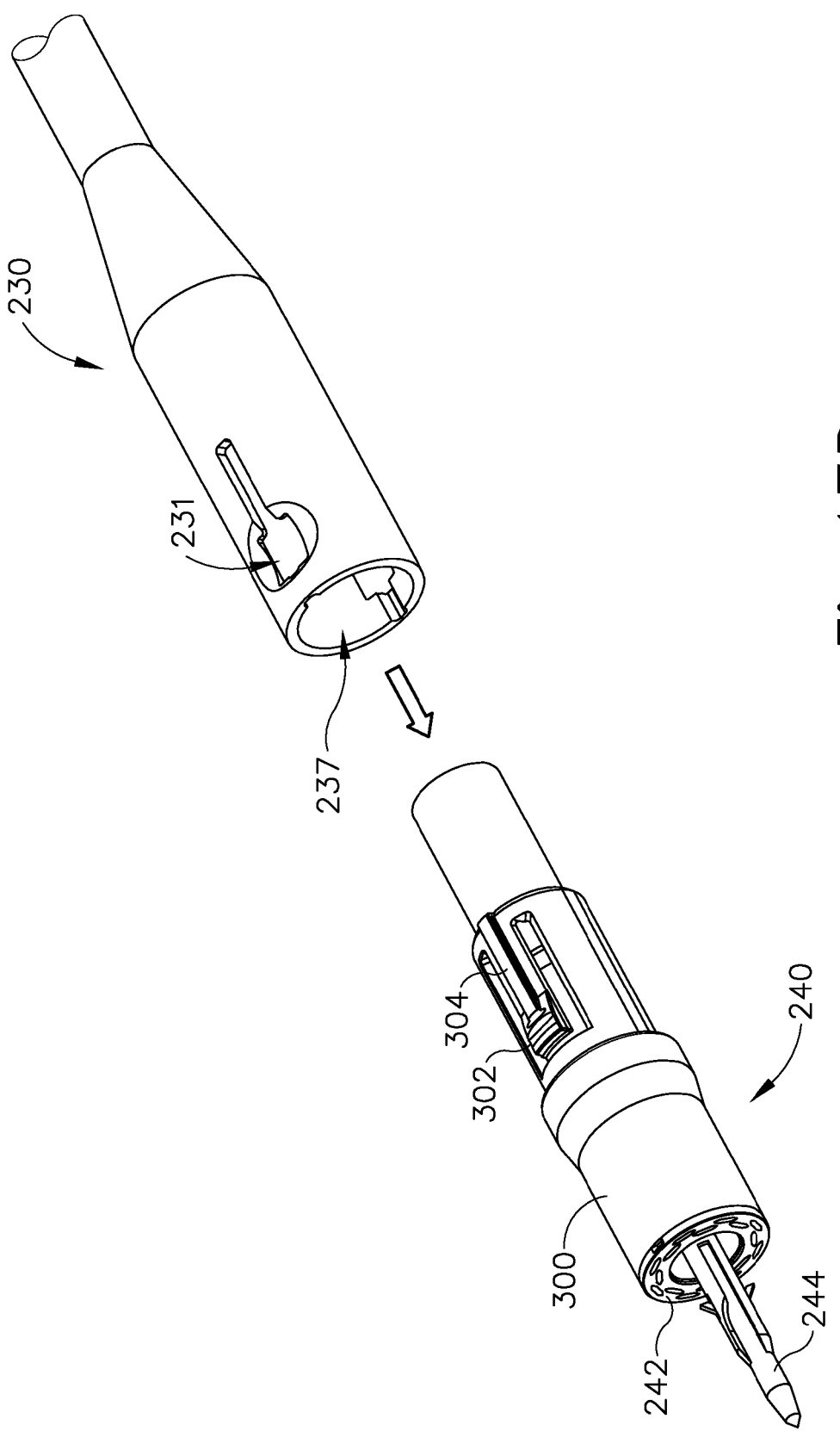

MOTOR DRIVEN ROTARY INPUT CIRCULAR STAPLER WITH MODULAR END EFFECTOR

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side elevation view of an exemplary circular stapling surgical instrument;

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 6 depicts an diagrammatic view of the indicator window of FIG. 5 showing an exemplary indicator bar and exemplary corresponding staple representations;

FIG. 17B depicts a perspective view of the stapling head assembly of FIG. 8, with the stapling head cartridge decoupled from the shaft assembly.

Figure 2A:
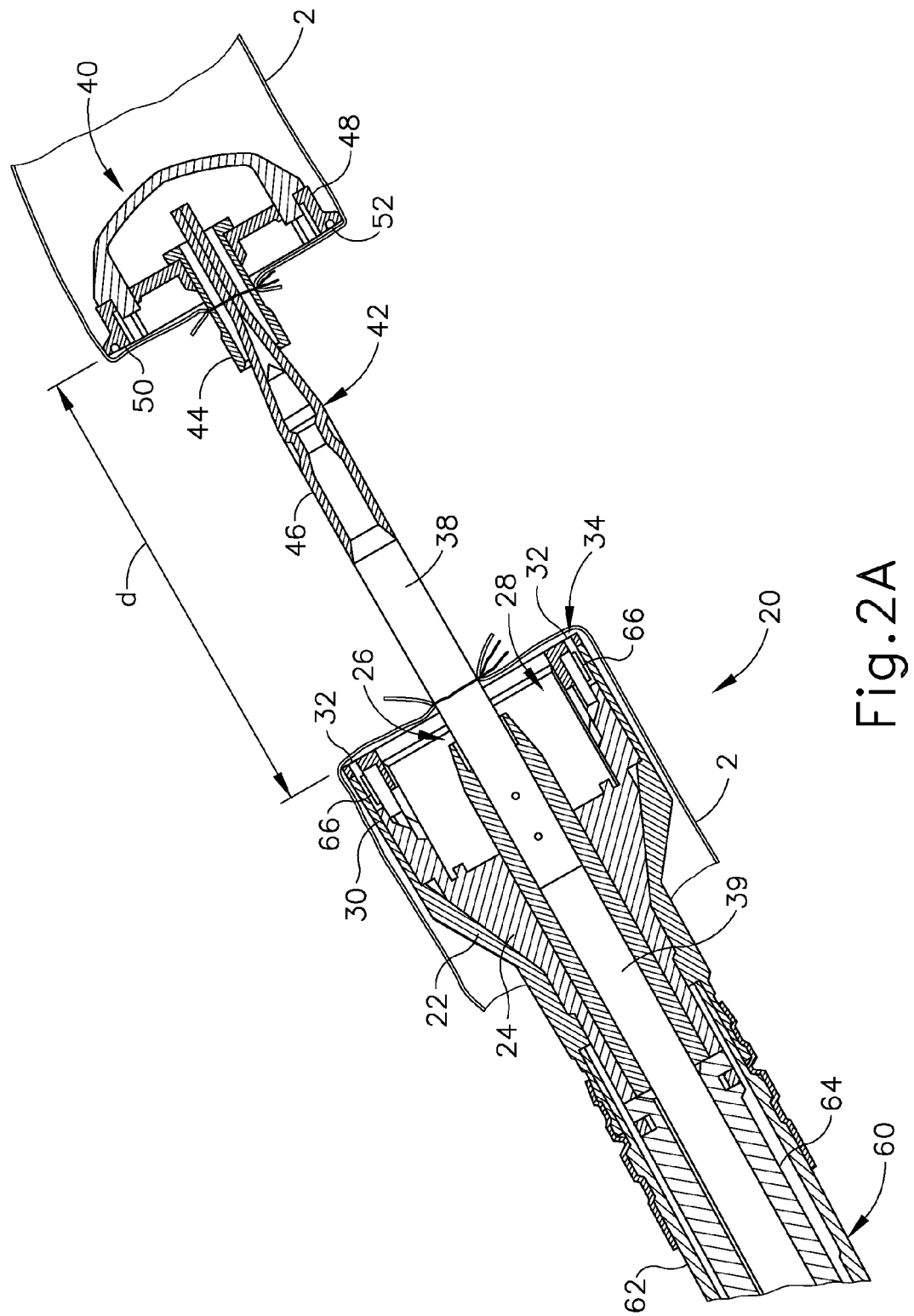
FIG. 2A depicts an enlarged longitudinal cross-section view of an exemplary stapling head assembly of the instrument of FIG. 1 showing an exemplary anvil in an open position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 2B:
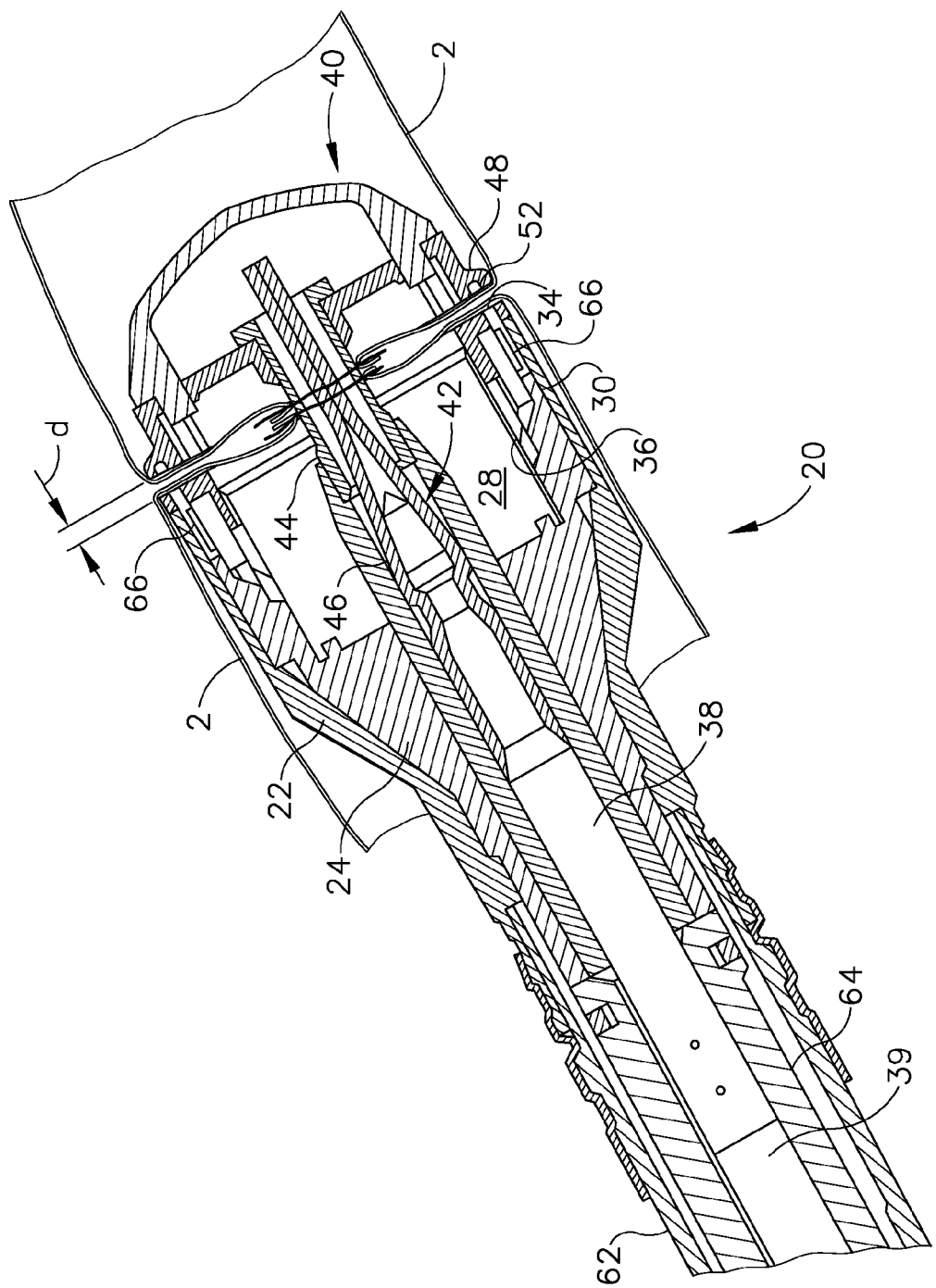
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
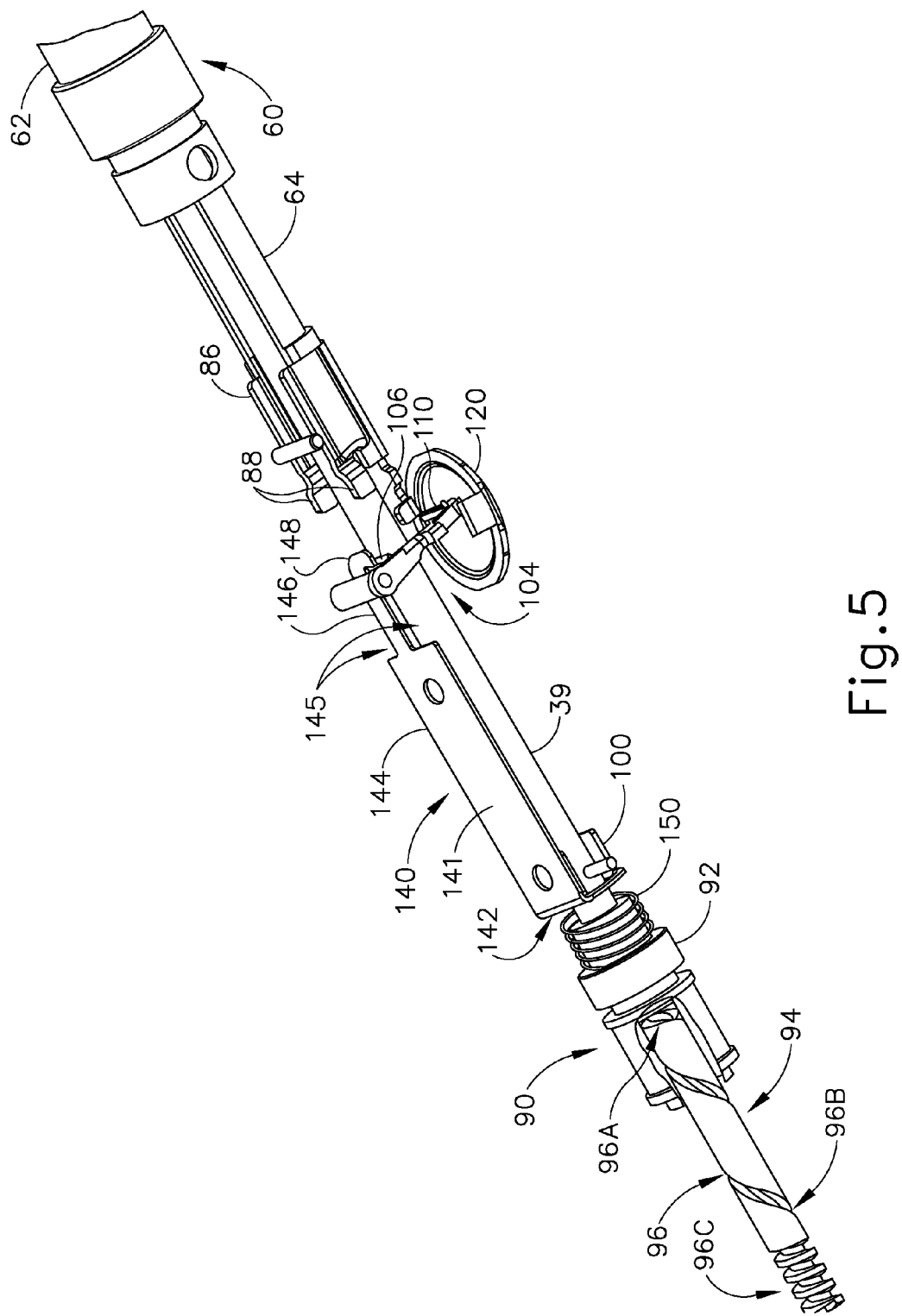
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
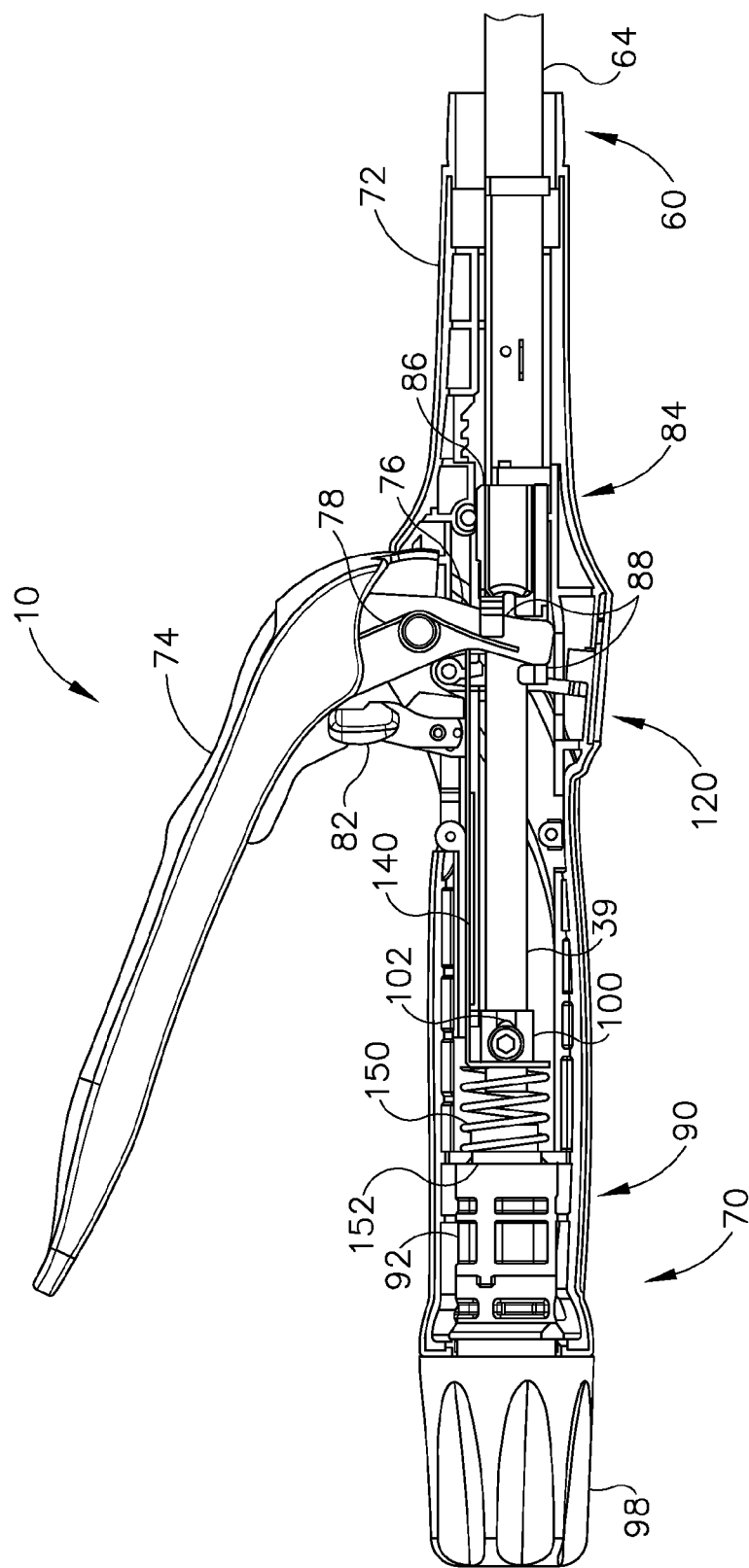
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
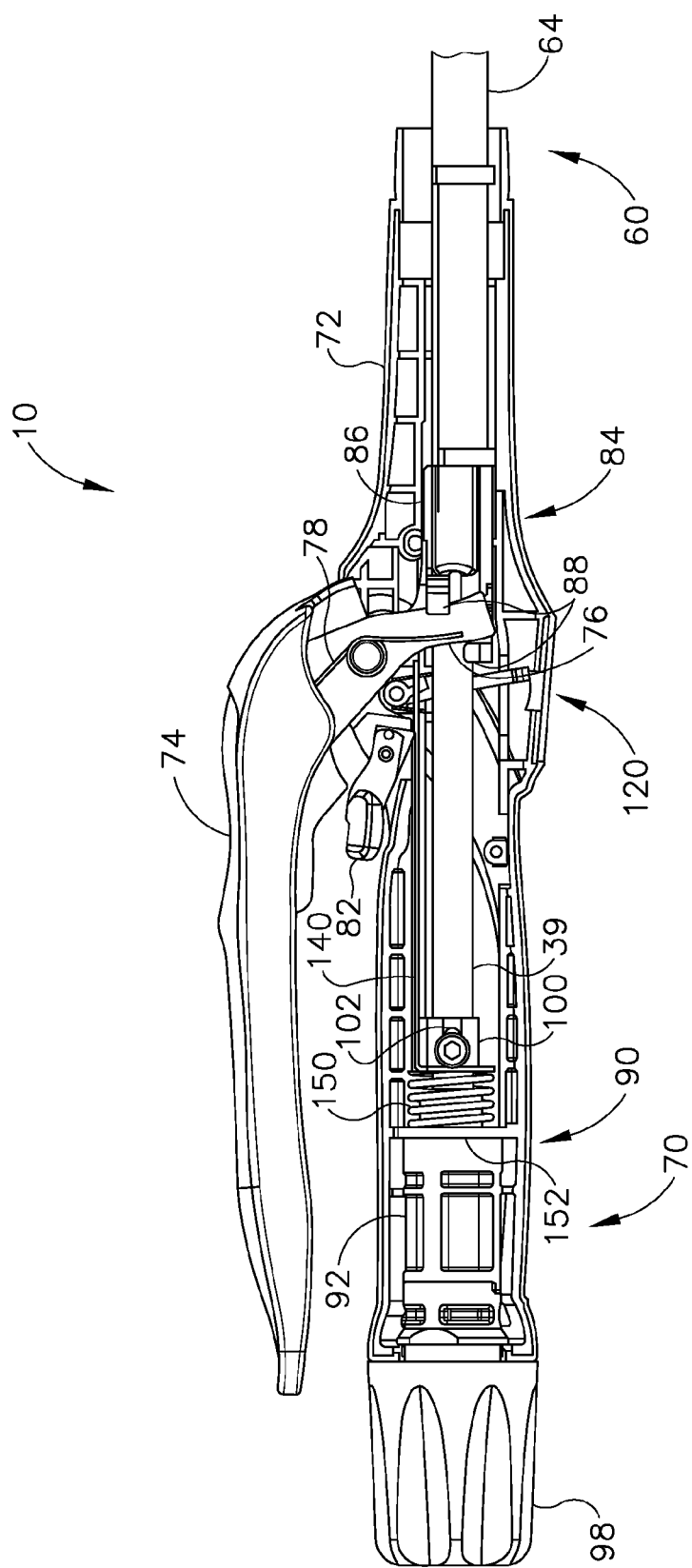
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjusting knob (98) is rotated. In some other versions, U-shaped clip (100) engages with a portion of body (72) to substantially prevent trocar actuator (39) from rotating about its axis when adjusting knob (98) is rotated. U-shaped clip (100) of the present example further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130)

(shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

II. Exemplary Motorized Circular Stapling Surgical Instrument with Selectable Control In some instances, it may be desirable to provide motorized control of instrument (10). It may further be desirable to enable a user to select between either motorized control or manual control of a motorized version of circular surgical stapling instrument (10). For example, instrument (10) may include an operational mode selection assembly that allows the user to disengage an automated, motorized rotary actuation system and provide manual actuation of that system. It may also be desirable to provide a switch assembly for changing the mode of a single rotary drive between a tissue clamping mode and a tissue cutting/stapling mode. In other words, such a switch assembly may enable a single rotary drive to either actuate anvil (40) clamping features or actuate knife (36) and staple driving features of instrument (10). The examples below include merely illustrative versions of instrument (10) where a single motor can be used to control both clamping and cutting/stapling of tissue via a single rotary drive; where the operator can select between motorized operation and manual operation; and a stapling head cartridge assembly that is responsive to the single rotary drive in motorized and manual operation.

Figure 7A:
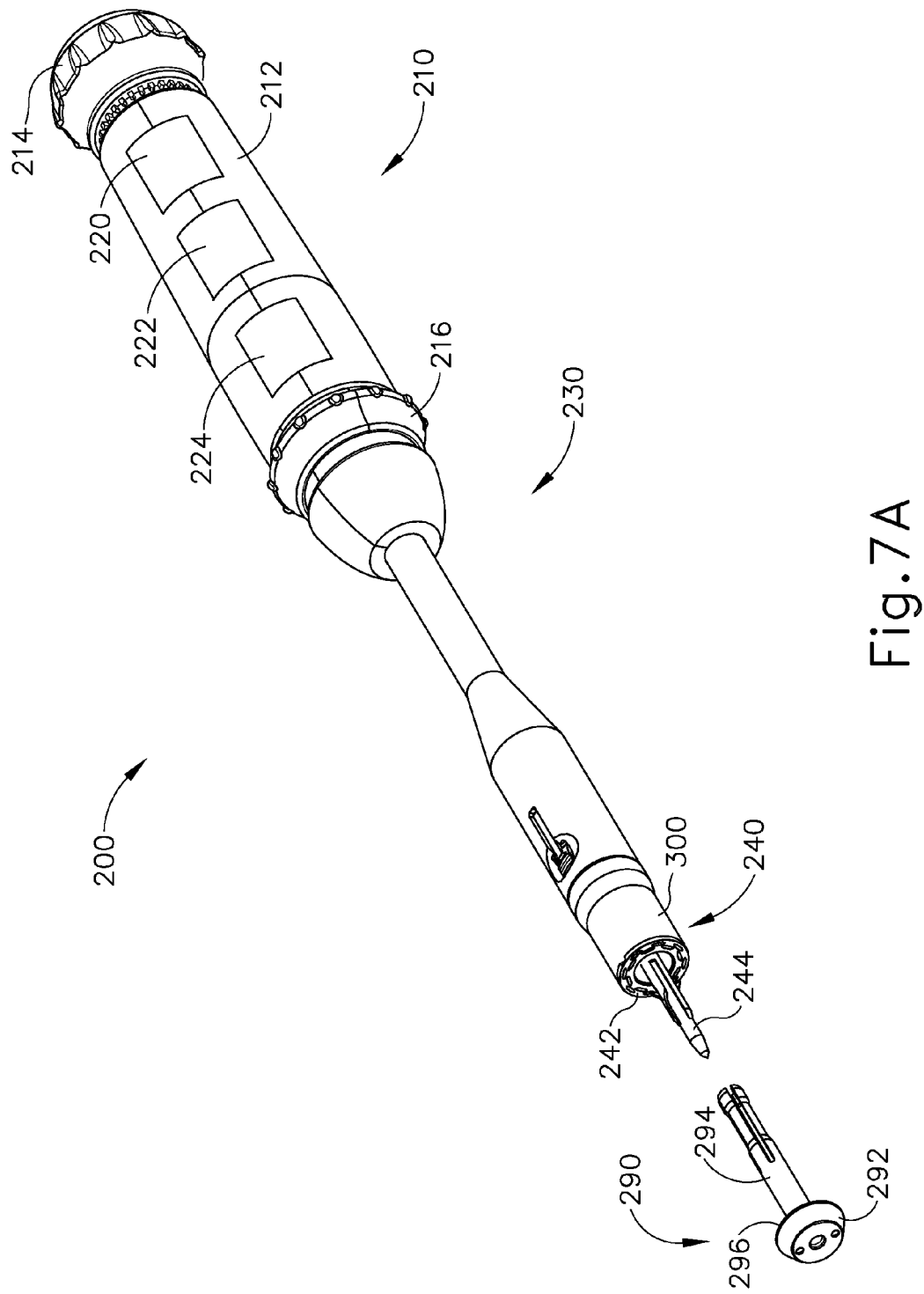
FIG. 7A depicts a perspective view of an exemplary alternative circular stapling surgical instrument, with an anvil decoupled from a trocar.
Figure 7B:
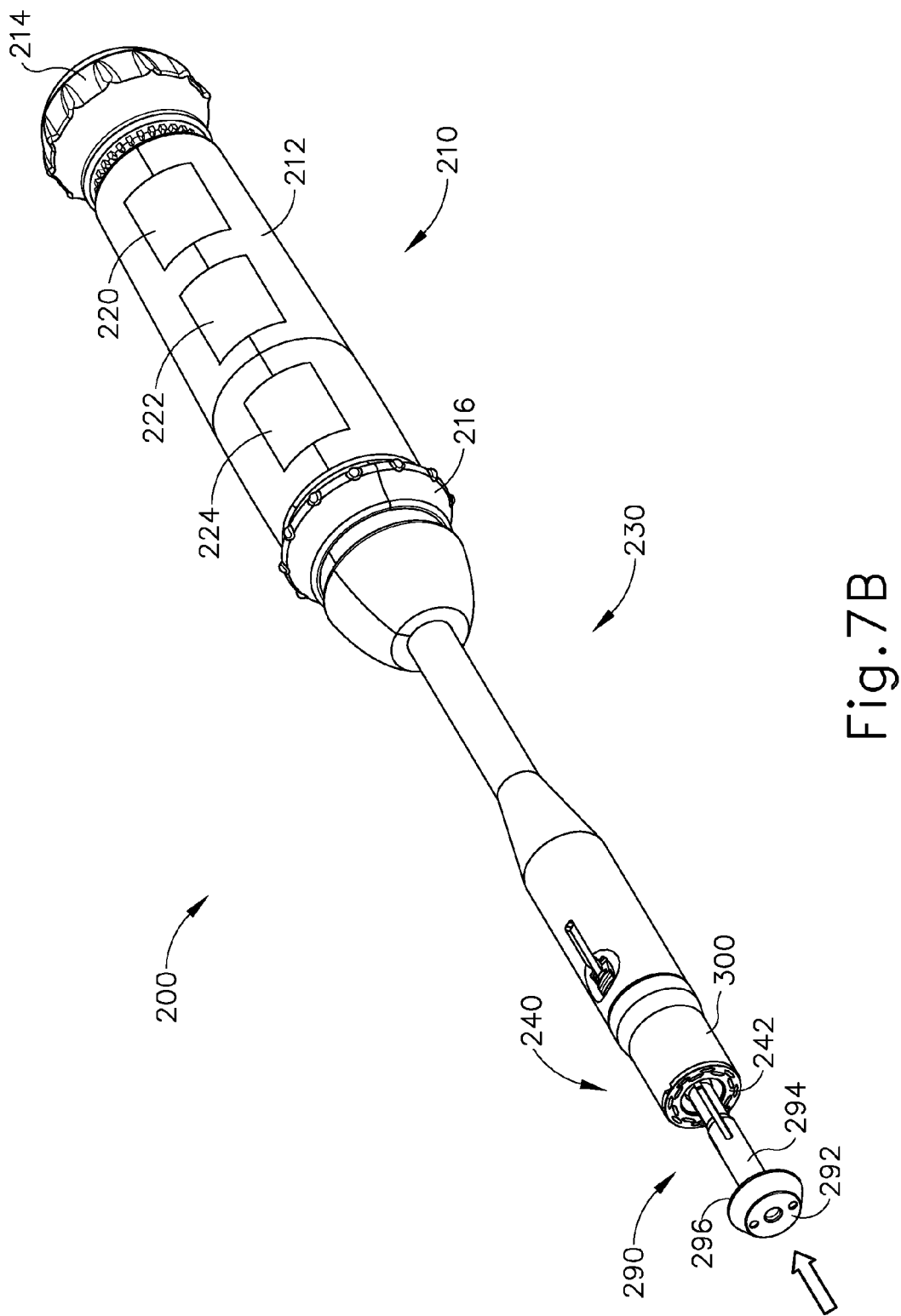
FIG. 7B depicts a perspective view of the surgical instrument of FIG. 7A, with the anvil coupled with the trocar.

FIGS. 7A-7B show an exemplary motorized stapling instrument (200) that serves as a variation of instrument (10). Stapling instrument (200) of this example includes a handle assembly (210), a shaft assembly (230), and a stapling head assembly (240). Like stapling head assembly (20) described above, stapling head assembly (240) of the present example is operable to couple with an anvil (290), clamp tissue with anvil (290), cut tissue clamped with anvil (290), and drive staples into tissue that is clamped with anvil (290). Stapling instrument (200) may be used to create a secure anastomosis (e.g., an end-to-end anastomosis) within a gastro-intestinal tract of a patient or elsewhere. Anvil (290) of this example includes a head (292), a shaft (294) extending proximally from head (294), and a proximal face (296) that presents concentric annular arrays of staple forming pockets (not shown). Shaft (294) is configured to removably couple with trocar (244) of stapling head assembly (240). Various exemplary features and operabilities of stapling head assembly (240) will be described in greater detail below; while other suitable features and operabilities will be apparent to those of ordinary skill in the art in view of the teachings herein.

Shaft assembly (230) is operable to communicate a rotary drive force from handle assembly (210) to stapling head assembly (240) via a rotary drive shaft (232) as will be described in greater detail below. Some versions of shaft assembly (230) may include one or more flexible sections. An example of a shaft assembly that is configured with flexible sections and that may be incorporated into shaft assembly (230) is disclosed in U.S. patent application Ser. No. 13/716,323, entitled "Motor Driven Rotary Input Circular Stapler with Lockable Flexible Shaft," filed on even date herewith, published as U.S. Pat. Pub. No. 2014/0166718 on Jun. 19, 2014, now U.S. Pat. No. 9,463,022, issued Oct. 11, 2016, the disclosure of which is incorporated by reference herein. Alternatively, shaft assembly (230) may be rigid along the length of shaft assembly (230) or have one or more flexible sections configured in some other fashion.

Handle assembly (210) includes an integral power source (220), a motor (222), and a transmission assembly (224). Integral power source (220) may comprise a rechargeable battery or a non-rechargeable battery. In some other versions, power source (220) is external to handle assembly (210). By way of example only, power source (220) may be located in shaft assembly (230), in stapling head assembly (240), or completely external to stapling instrument (200). Motor (222) may comprise a conventional DC motor. Transmission assembly (224) is coupled with motor (222) and with a proximal end (233) of rotary drive shaft (223); and is operable to communicate rotary motion from motor (222) to rotary drive shaft (232). Transmission assembly (224) is also operable to communicate this rotary motion regardless of whether rotary drive shaft (232) is shifted longitudinally to a distal position or shifted longitudinally to a proximal position, as will be described in greater detail below.

Handle assembly (210) also includes a rotary control knob (214) and a control ring (216). Rotary control knob (214) is operable to translate longitudinally to select between motorized operation of stapling instrument (200) or manual operation of stapling instrument (200). Rotary control knob (214) is also rotatable to manually rotate drive shaft (232) when rotary control knob (214) is in the manual operation longitudinal position. Control ring (216) is longitudinally movable to move drive shaft (232) between the distal position and the proximal position. By way of example only, at least some of handle assembly (210) may be configured and operable in accordance with at least some of the teachings of U.S. patent application Ser. No. 13/716,308, entitled "Circular Stapler with Selectable Motorized and Manual Control," filed on even date herewith, published as U.S. Pat. Pub. No. 2014/0166727 on Jun. 19, 2014, now U.S. Pat. No. 9,445,816, issued Sep. 20, 2016, the disclosure of which is incorporated by reference herein. Other suitable ways in which handle assembly (270) may be constructed and operable will be apparent to those of ordinary skill in the art in view of the teachings herein. It should also be understood that the teachings herein are not limited to stapling instruments that have motors. Indeed, the teachings below may be readily applied to various kinds of instruments that are purely manually operated and that do not even provide an option of motorized operation.

A. Exemplary Drive Stapling Head Drive Assembly

FIGS. 8-15 show various features that are used to drive stapling head assembly (240) of the present example. In particular, these features include a first rotary drive element (250), a second rotary drive element (260), a drive nut (270), and a clamping driver (280). These components (250, 260, 270, 280) are coaxially aligned with drive shaft (232) and are all housed within a cartridge housing (300), which will be described in greater detail below. As can also be seen in FIG. 8, stapling head assembly (240) includes staple deck (242), a staple driver (243), and a cylindraceous knife (245). Staple driver (243) is operable to translate distally to drive staples (not shown) through openings in staple deck (242) and into staple forming pockets of proximal face (296) of anvil (290). Knife (245) translates distally with staple driver (243), thereby cutting tissue at substantially the same time that the adjacent tissue is being stapled.

Figure 9:
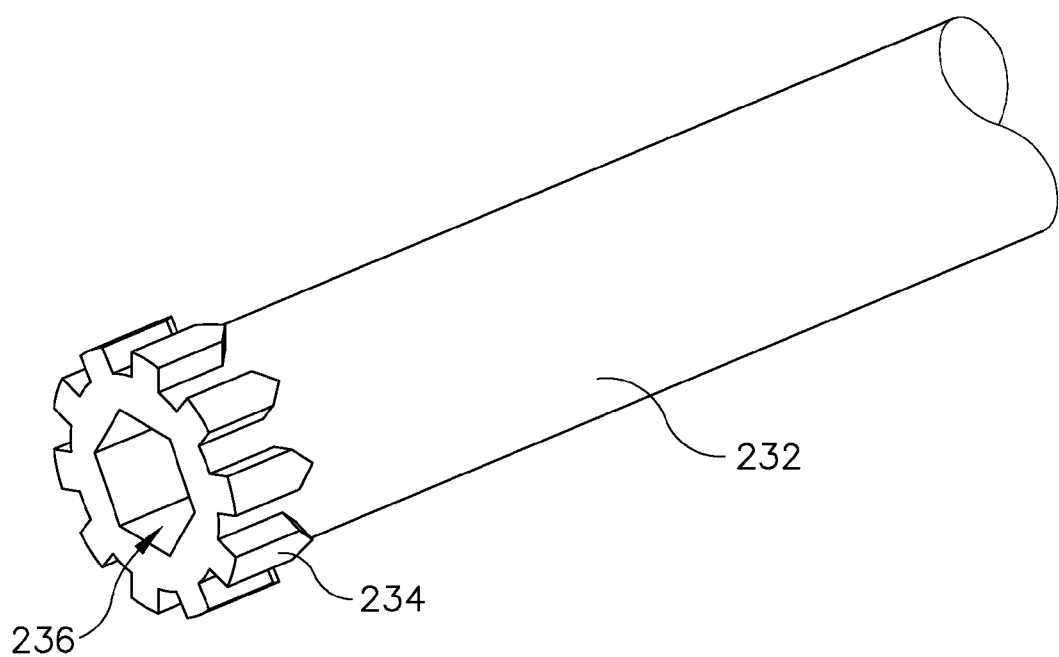
FIG. 9 depicts a partial perspective view of the distal end of the rotary drive shaft of the surgical instrument of FIG. 7A.
Figure 10:
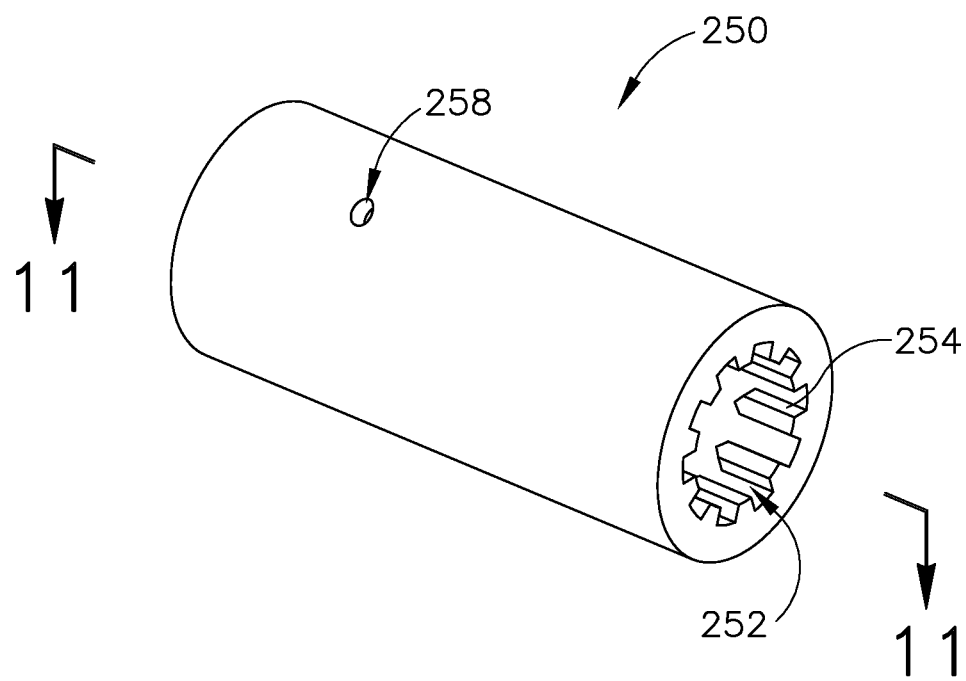
FIG. 10 depicts a perspective view of a first rotary drive element of the stapling head assembly of FIG. 8.
Figure 11:
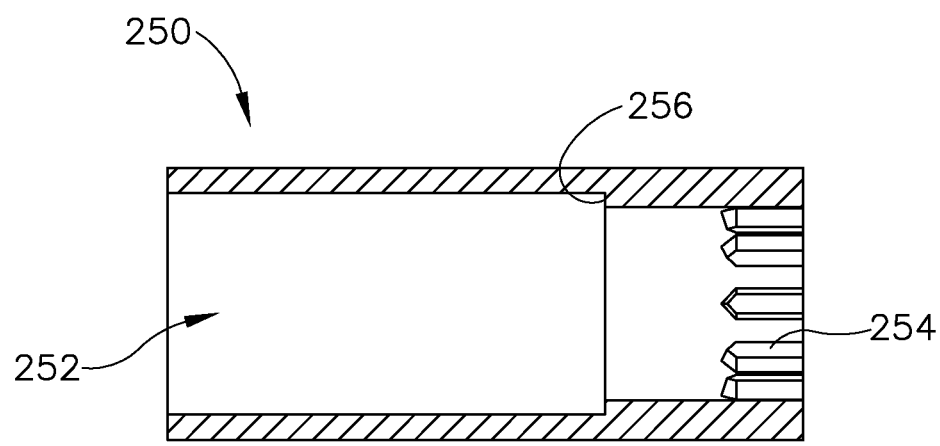
FIG. 11 depicts a cross-sectional view of the first rotary drive element of FIG. 10, taken along line 11-11 of FIG. 10.

As best seen in FIGS. 10-11, first rotary drive element (250) defines a bore (252) and includes a proximal set of inner splines (254). The diameter of bore (252) increases distal to inner splines (254), such that first rotary drive element (250) includes a distally facing annular shoulder (256). First rotary drive element (250) also includes a threaded opening (258) that extends transversely from the exterior of first rotary drive element (250) into bore (252). As shown in FIG. 9, the distal end of drive shaft (232) includes a set of outer splines (234) that complement inner splines (254) of first rotary drive element (250). Thus, when splines (234, 254) are at a common longitudinal position, rotation of drive shaft (232) rotates first rotary drive element (250). In the present example, splines (234, 254) are at a common longitudinal position when drive shaft (232) is in a proximal position. When drive shaft (232) is driven to a distal position (e.g., by sliding control ring (216) distally), splines (234, 235) disengage such that rotation of drive shaft (232) will not rotate first rotary drive element (250). As shown in FIGS. 9-11, splines (234, 254) have complementary tapered ends to promote positioning of splines (234) in the interstices between splines (254) when drive shaft (232) is translated back from the distal position to the proximal position.

Figure 12:
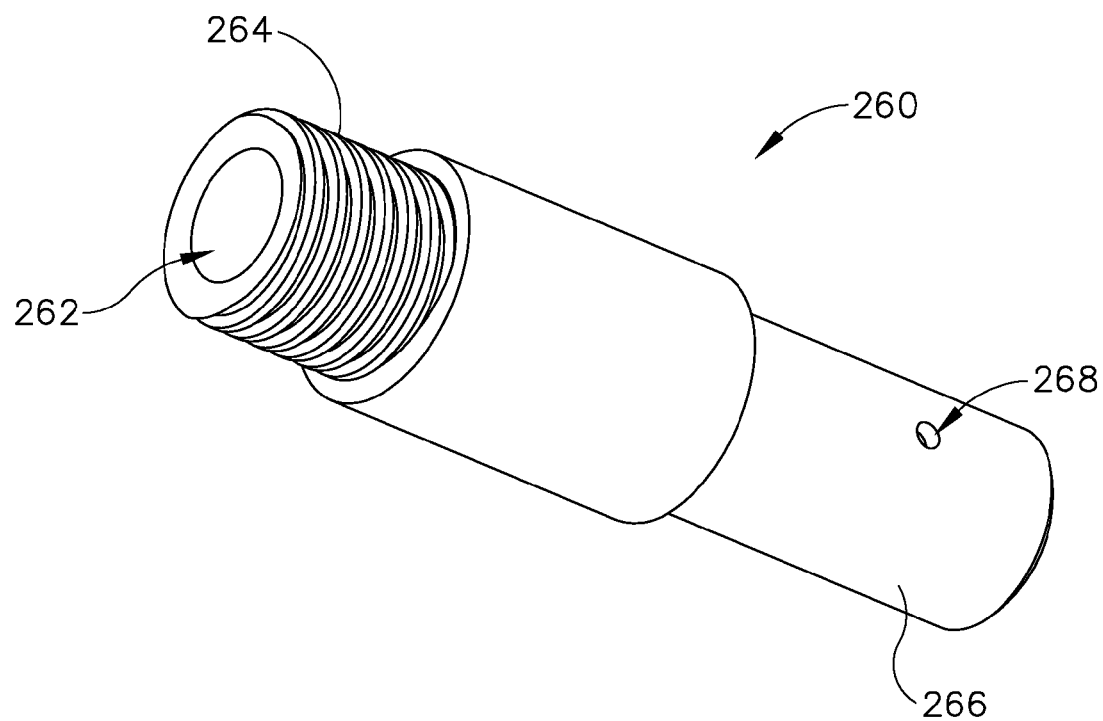
FIG. 12 depicts a perspective view of a second rotary drive element of the stapling head assembly of FIG. 8.

As best seen in FIG. 12, second rotary drive element (260) of the present example defines an inner bore (262), includes outer threading (264) at its distal end, and includes a necked-down proximal portion (266). A threaded opening (268) extends transversely from the exterior of second rotary drive element (260) into bore (262). Proximal portion (266) is configured to slidably fit within bore (262) of first rotary drive element (250). In particular, threaded openings (258, 268) align with each other when proximal portion (266) is disposed in bore (262), and a set screw (251) (shown in FIG. 8) is secured in threaded openings (258, 268) to secure first and second rotary drive elements (250, 260) together. First and second rotary drive elements (250, 260) will thus rotate together unitarily.

Figure 8:
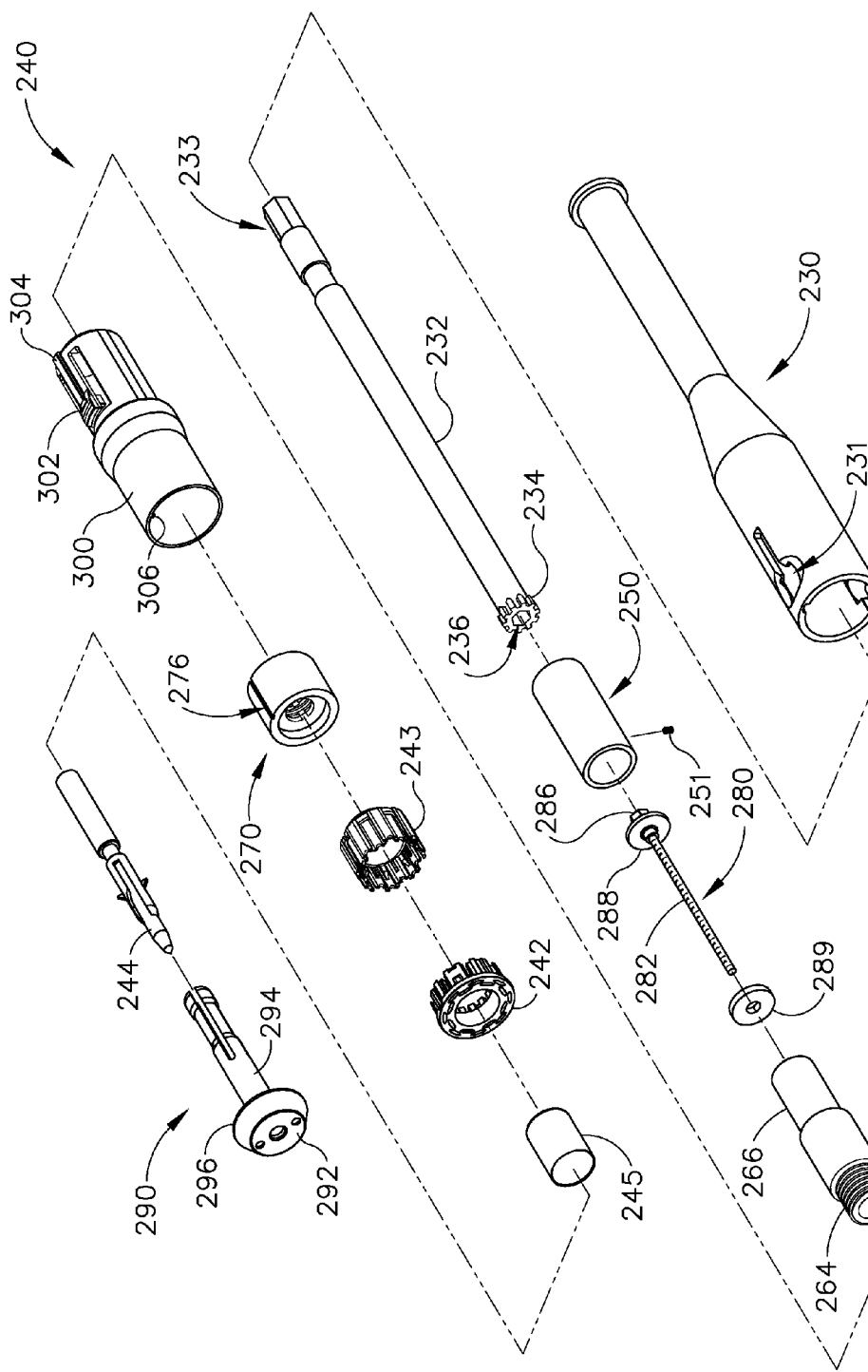
FIG. 8 depicts a partially exploded view of the surgical instrument of FIG. 7A, showing components of the stapling head assembly.
Figure 13:
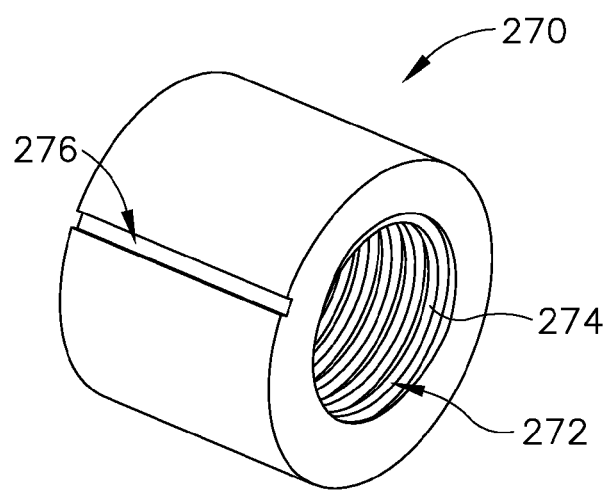
FIG. 13 depicts a perspective view of a drive nut of the stapling head assembly of FIG. 8.

As best seen in FIG. 13, drive nut (270) of the present example defines an inner bore (262), includes an inner threading (274), and includes an outer keyway (276). Bore (262) is configured to receive the distal end of second rotary drive element (260). In particular, threading (264) meshes with threading (274). Outer keyway (276) receives a key (306) that extends inwardly from cartridge housing (300) (as shown in FIG. 8). The relationship between keyway (276) and key (306) prevents drive nut (270) from rotating relative to cartridge housing (300); but permits drive nut (270) to translate relative to cartridge housing (300). It should therefore be understood that, when drive shaft (232) and rotary drive elements (250, 260) rotate together, the relationship between threading (264, 274) will cause drive nut (270) to translate distally or proximally within cartridge housing (300), depending on the direction in which drive shaft (232) and rotary drive elements (250, 260) are rotated. Staple driver (243) and knife (245) are fixedly secured to drive nut (270) in this example, such that staple driver (243) and knife (245) translate unitarily with drive nut (270) relative to staple deck (242) and relative to cartridge housing (300). It should therefore be understood that, when drive shaft (232) is at a proximal position and is rotated, such rotation will drive staple driver (243) and knife (245) distally or proximally relative to staple deck (242) and relative to cartridge housing (300), depending on the direction of rotation.

Figure 14:
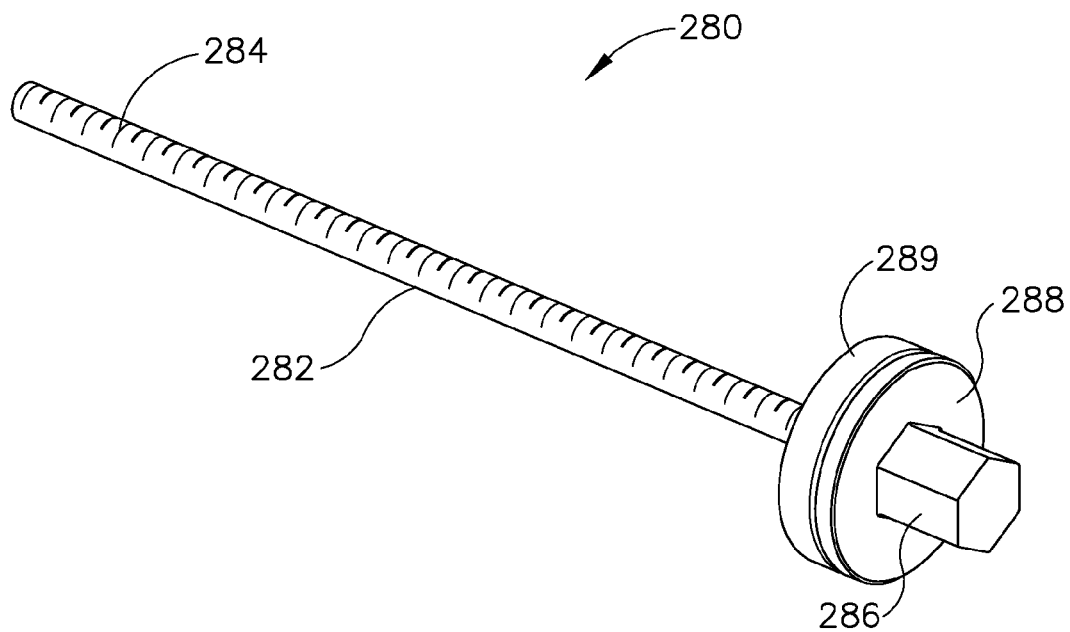
FIG. 14 depicts a perspective view of a clamping driver of the stapling head assembly of FIG. 8.
Figure 15:
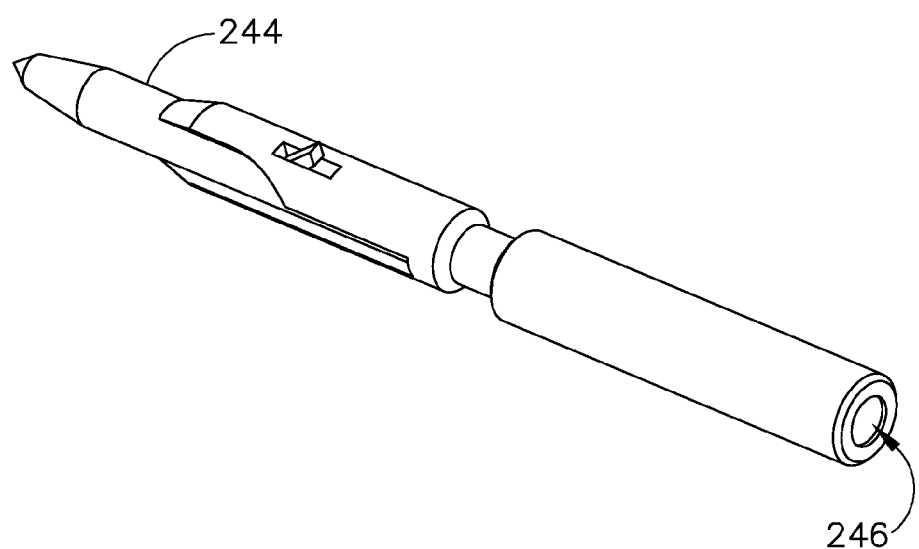
FIG. 15 depicts a perspective view of the trocar of the stapling head assembly of FIG. 8.

As best seen in FIG. 14, clamping driver (280) of the present example comprises a shaft (282) with threading (284) at the distal end of shaft (282). Clamping driver (280) also includes a proximal drive feature (286), an annular flange (288), and a thrust bearing (289) that is positioned about shaft (282) and distal to annular flange (288). As best seen in FIGS. 16A-16D, shaft (282) extends longitudinally through bores (252, 262, 272) to reach trocar (244). As best seen in FIG. 15, the proximal end of trocar (244) includes a threaded opening (246). Threaded opening (246) is configured to receive the distal end of shaft (282), thereby meshing with threading (284). Trocar (244) is operable to translate relative to cartridge housing (300) but not rotate relative to cartridge housing (300). Thus, trocar (244) will translate relative to cartridge housing (300) in response to rotation of clamping driver (280) relative to cartridge housing (300), due to interaction between threading (284) and threaded opening (246). As can also be seen in FIGS. 16A-16D, flange (288) and thrust bearing (289) are captured between shoulder (256) of first rotary drive element (250) and the proximal end (266) of second rotary drive element (260), such that rotary drive elements (250, 260) prevent clamping driver (280) from moving longitudinally.

Proximal drive feature (286) has a hexagonal cross-section in this example, and is thus configured to complement a hexagonal recess (236) formed at the distal end of drive shaft (232) as shown in FIG. 9. While hexagonal shapes are used in the present example, it should be understood that any other suitable shape may be used, including but not limited to rectangular, semicircular, triangular, elliptical, etc. When drive shaft (232) is at the distal position (e.g., when control ring (216) is in the distal position), proximal drive feature (286) is received in hexagonal recess (236), such that rotation of drive shaft (232) rotates clamping driver (280). When drive shaft (232) is at the proximal position (e.g., when control ring (216) is in the proximal position), proximal drive feature (286) is disengaged from hexagonal recess (236), such that rotation of drive shaft (232) does not rotate clamping driver (280).

B. Exemplary Sequence of Operation

It should be understood from the foregoing that, when drive shaft (232) is at the distal position, rotation of drive shaft (232) will rotate clamping driver (280) but not rotary drive elements (250, 260). When drive shaft (232) is in the proximal position, rotation of drive shaft (232) will rotate rotary drive elements (250, 260) but not clamping driver (280). Thus, drive shaft (232) may be rotated and translated in a particular sequence to provide clamping, cutting, and stapling of tissue. An example of such a sequence is shown in FIGS. 16A-16D.

Figure 16A:
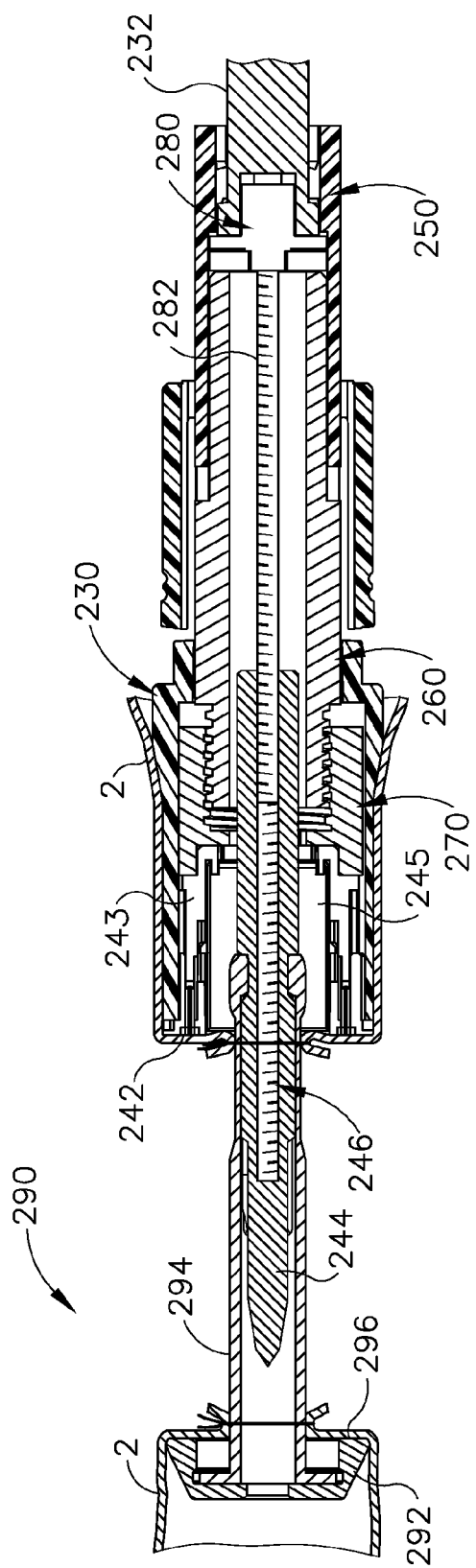
FIG. 16A depicts a cross-sectional side view of the stapling head assembly of FIG. 8, with the anvil in an open position and with the rotary drive shaft in a distal position.

In particular, FIG. 16A shows anvil (290) coupled with trocar (244) and drive shaft (232) in the distal position. It should be understood that control ring (216) is also in the distal position at this stage. Head (292) of anvil (290) is positioned in a first lumen (400) defined by tissue (402), with shaft (294) of anvil (290) protruding from lumen (400). A suture (404) is used to secure tissue (402) about shaft (294) in a purse-string fashion. In some uses, tissue (402) defines an upper section of a gastrointestinal tract, such as an upper colon portion or an upper esophagus portion. It should be understood that anvil (290) may travel proximally through lumen (400) before being coupled with trocar (244). Stapling head assembly (240) is positioned within a second lumen (410) defined by tissue (412). A suture (414) is used to secure tissue (412) about trocar (244) in a purse-string fashion. In some uses, tissue (412) defines a lower section of a gastrointestinal tract, such as a lower colon portion or a lower esophagus portion. It should be understood that stapling head assembly (240) may travel distally through lumen (410) before being coupled with anvil (290).

Figure 16B:
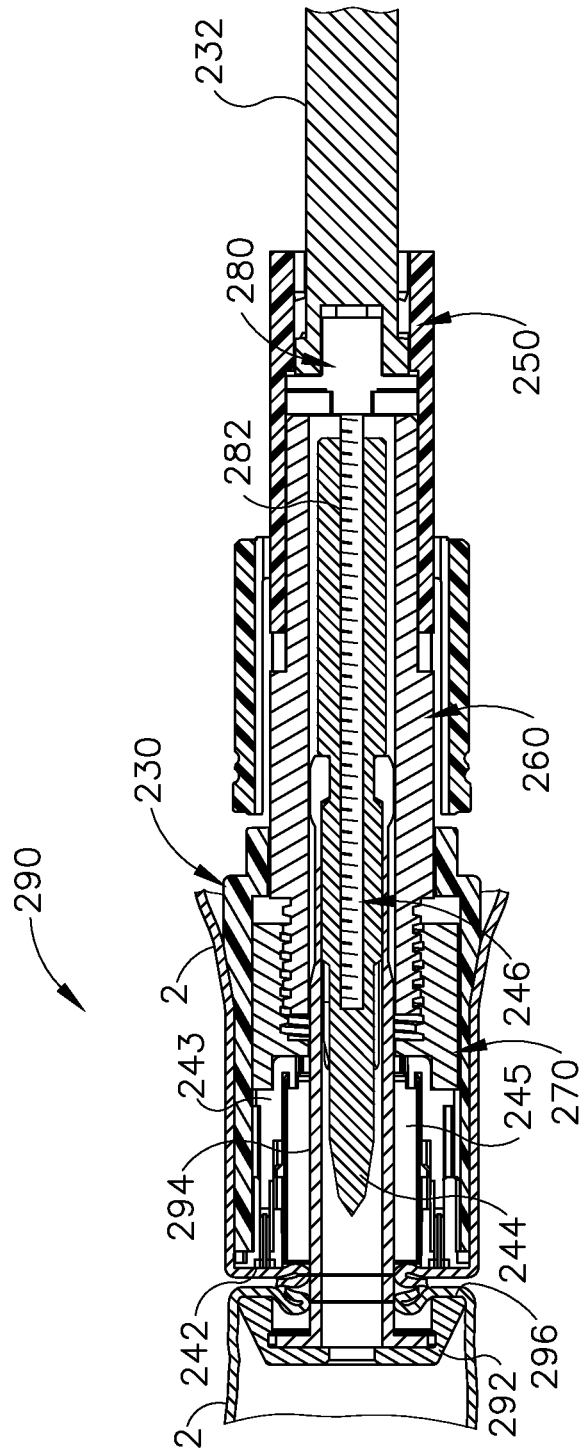
FIG. 16B depicts a cross-sectional side view of the stapling head assembly of FIG. 8, with the anvil in a closed position and with the rotary drive shaft in the distal position.

With anvil (290) and stapling head assembly (240) coupled and positioned within respective lumens (400, 410), motor (222) may be activated to rotate drive shaft (232). If handle assembly (210) is in manual operation mode, control knob (214) may be manually rotated to rotate drive shaft (232). With drive shaft (232) being in the distal position, drive feature (286) of clamping driver (280) is seated in recess (236) of drive shaft (232), such that rotation of drive shaft (232) rotates clamping driver (280). This rotation retracts trocar (244) and anvil (290) proximally relative to stapling head assembly (240) as shown in FIG. 16B. This retraction provides clamping of tissue (402, 412) between proximal face (296) of anvil head (292) and staple deck (242). Drive shaft (232) may be rotated until the desired gap between proximal face (296) and staple deck (242) is achieved. The gap may be indicated to the user in numerous ways. By way of example only, stapling instrument (200) may include an equivalent of indicator window (120) as described above. As another merely illustrative example, an encoder or other feature may track rotation of drive shaft (232) and a control module may read such data and accordingly drive an LED display or other type of electronic display to indicate the gap distance to the user. Other suitable ways in which an operator may receive gap distance feedback will be apparent to those of ordinary skill in the art in view of the teachings herein.

Figure 16C:
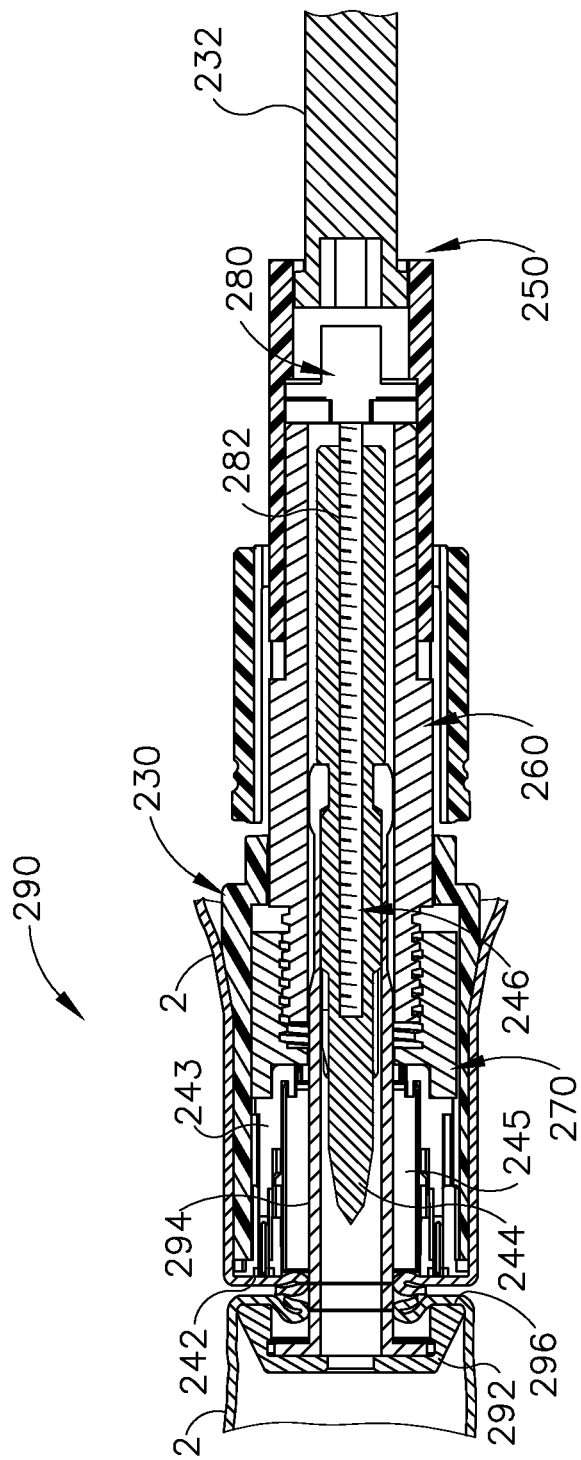
FIG. 16C depicts a cross-sectional side view of the stapling head assembly of FIG. 8, with the anvil in the closed position and with the rotary drive shaft shifted to a proximal position.

Once the operator has achieved the desired gap between proximal face (296) and staple deck (242), the user may translate drive shaft (232) proximally as shown in FIG. 16C. This may be done by translating control ring (216) proximally or in any other suitable fashion. When drive shaft (232) translates proximally (232), recess (236) disengages drive feature (286) and splines (234) engage splines (254). The translation of drive shaft (232) from the distal position to the proximal position thus shifts stapling head assembly (240) from a tissue clamping mode to a tissue cutting/stapling mode. In some other versions, stapling head assembly (240) is configured such that translating drive shaft from the distal position to the proximal position shifts stapling head assembly (240) from a tissue cutting/stapling mode to a tissue clamping mode; and vice-versa.

Figure 16D:
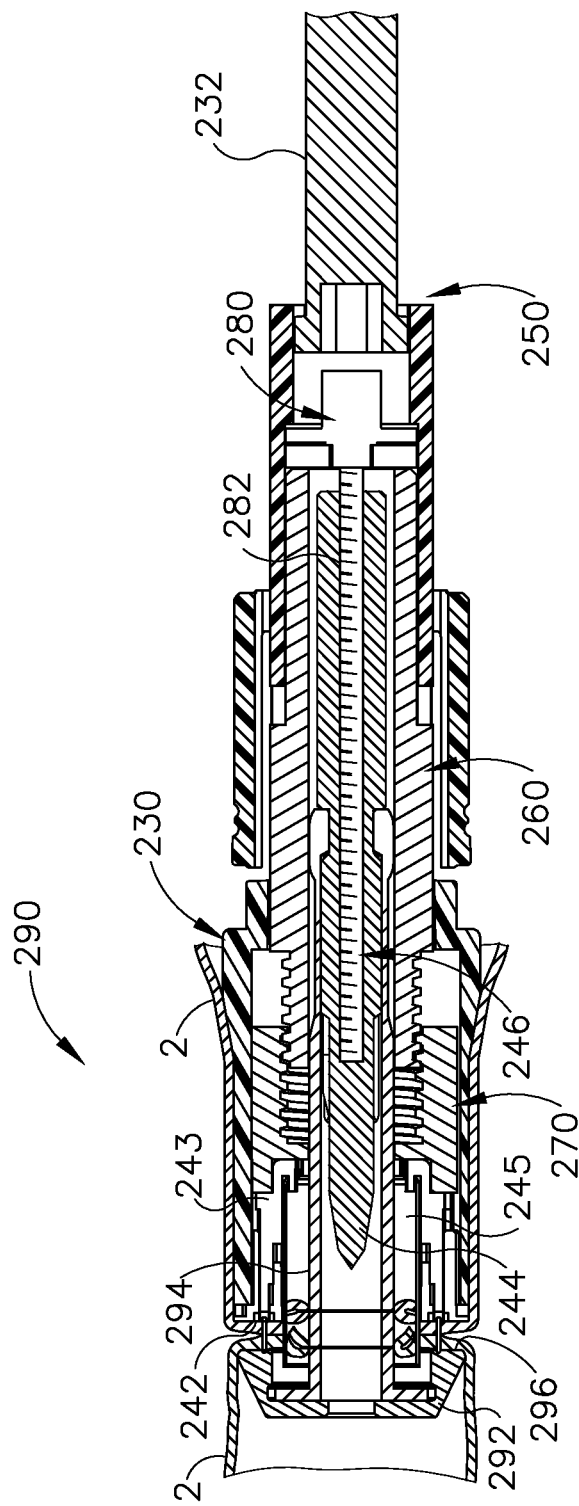
FIG. 16D depicts a cross-sectional side view of the stapling head assembly of FIG. 8, with the staple driver and blade in a fired position.

Once stapling head assembly (240) is shifted from tissue clamping mode to tissue cutting/stapling mode, drive shaft (232) may again be rotated. Again, this may be accomplished by activating motor (222); or by rotating control knob (214) manually if handle assembly (210) is in manual operation mode. In some instances, an operator may prefer to use handle assembly (210) in manual operation mode during tissue clamping (FIGS. 16A-16B), and then use handle assembly (210) in motorized mode during tissue cutting/stapling (FIGS. 16C-116); or vice versa. In either case, when drive shaft (232) is rotated during tissue cutting/stapling mode, this rotation is communicated through rotary drive elements (250, 260). The rotation of rotary drive elements (250, 260) drives drive nut (270) distally as shown in FIG. 16D, due to engagement between threading (264, 274). This distal advancement of drive nut (270) advances staple driver (243), and knife (245) distally, thereby cutting and stapling tissue (402, 412). An encoder, force sensor, timer, and/or any other suitable feature may be used determine when to stop motor (222) automatically upon sufficient advancement of drive nut (270), staple driver (243), and knife (245).

After tissue (402, 412) has been stapled and cut, drive shaft (232) may be advanced distally again to engage clamping driver (280), then rotated in the opposite direction to drive anvil (290) slightly away from stapling head assembly (240). With anvil (290) still coupled with stapling head assembly (240), stapling instrument (200) may then be withdrawn proximally through lumen (410), leaving a secure and fluid tight anastomosis joining lumens (400, 410) together. Other suitable ways in which stapling instrument (200) may be used will be apparent to those of ordinary skill in the art in view of the teachings herein.

C. Exemplary Removable Stapling Head Cartridge

Figure 17A:
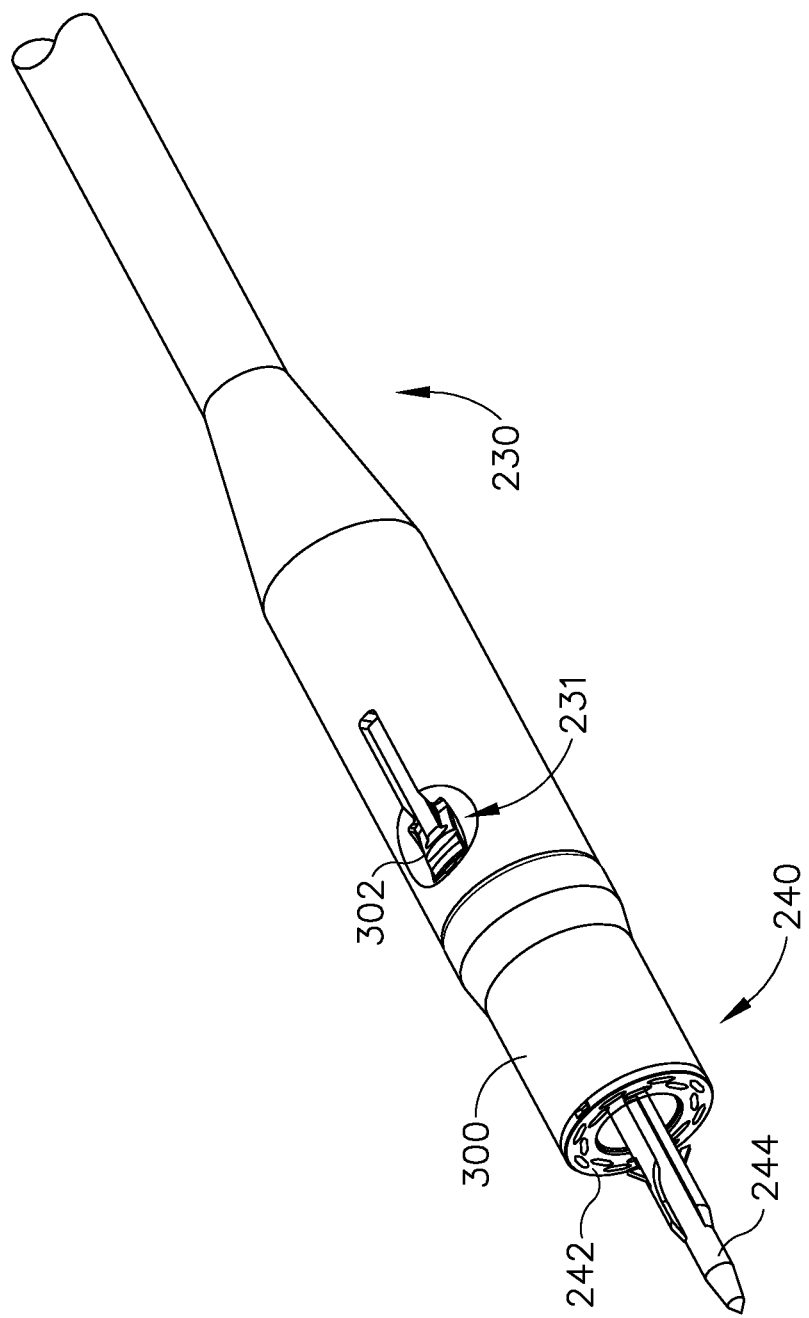
FIG. 17A depicts a perspective view of the stapling head assembly of FIG. 8, with the stapling head cartridge coupled with the shaft assembly.
Figure 18:
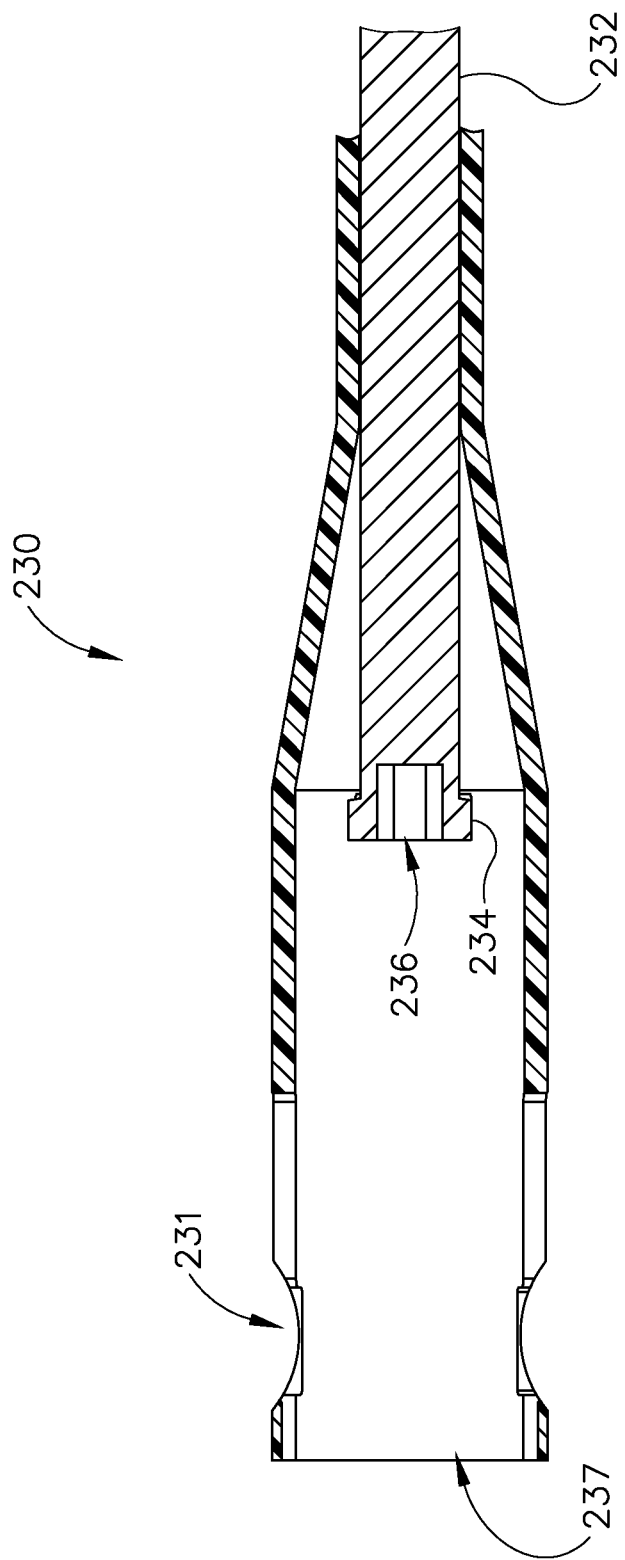
FIG. 18 depicts a cross-sectional view of the distal end of the shaft assembly of the surgical instrument of FIG. 7A.

In some instances, it may be desirable to permit removal of at least part of stapling head assembly (240) from the rest of stapling instrument (200). FIGS. 17-18 show exemplary features that are incorporated into stapling head assembly (240) and shaft assembly (230) of the present example to enable removal of stapling head assembly (240) from shaft assembly (230). In particular, FIGS. 17-18 show stapling head assembly (240) being provided in a cartridge housing (300) that is removable from the distal end of shaft assembly (230). Cartridge housing (300) includes a pair of outwardly extending tabs (302) that are positioned at the free ends of respective resilient arms (304). The distal end of shaft assembly (230) presents a socket (237) that receives cartridge housing (300). Socket (237) includes a pair of lateral openings (231) that correspond with tabs (302) of cartridge housing (302). In particular, resilient arms (304) are configured to resiliently bias tabs (302) into openings (231) when cartridge housing (300) is fully seated in socket (237), thereby locking cartridge housing (300) in place relative to shaft assembly (230). As best shown in FIG. 18, the distal end of drive shaft (232) is positioned within socket (237), such that the distal end of drive shaft (232) will enter bore (252) of first rotary drive element (250) when cartridge housing (300) is fully seated in socket (237).

In order to remove cartridge housing (300) from socket (237), and thereby decouple stapling head assembly (240) from shaft assembly (230), a user may depress both tabs (302) inwardly to decouple tabs (302) from openings (231). While holding tabs (302) in these depressed positions, the user may then pull cartridge housing (300) distally away from shaft assembly (230) as shown in the transition from FIG. 17A to FIG. 17B. At some point thereafter, another cartridge housing (300) may be inserted into socket (237). In some instances, this may be performed during a single surgical procedure. For instance, if the operator made a mistake during an initial attempt at securing an anastomosis and failed to properly deploy staples from stapling head assembly (240), the operator may withdraw stapling head assembly from the surgical site and re-load shaft assembly (230) with another stapling head assembly (240) to try completing the anastomosis again with the same stapling instrument (200). The operator would thus avoid the need to dispose of the entire stapling instrument (200) and use a completely new stapling instrument (200).

As another merely illustrative example, stapling instrument (200) may be provided as a partially reusable device. For instance, after being used in a surgical procedure, a nurse or other personnel may remove stapling head assembly (240) from shaft assembly (230) and dispose of the used stapling head assembly (240). The rest of stapling instrument (200) may then be sent to a sterilization process or other reclamation process. In instances where stapling instrument (200) includes a power source (220), motor (222), and/or other electronic components, such components may be removed for separate processing while the remainder of shaft assembly (230) and handle assembly (210) are sterilized in any suitable fashion. After processing, the previously used shaft assembly (230) and handle assembly (210) may be combined with a new stapling head assembly (240) for use in another surgical procedure. Various other suitable ways in which components of stapling instrument (200) may be handle before, during, and after surgical procedures will be apparent to those of ordinary skill in the art in view of the teachings herein.

Of course, the modular cartridge configuration of stapling head assembly (240) in the present example is merely optional. Other suitable ways in which at least part of stapling head assembly (240) may be provided in a cartridge or modular form will be apparent to those of ordinary skill in the art in view of the teachings herein. It should also be understood that some versions of stapling head assembly (240) may simply be unitary with shaft assembly (230), such that stapling head assembly (240) may not be removed from shaft assembly (230). By way of example only, some such versions of stapling instrument (200) may be configured for a single use only, such that the entire stapling instrument (200), including stapling head assembly (240), is disposed of after a single use. Other suitable variations will be apparent to those of ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/693,430, entitled "Trans-Oral Circular Anvil Introduction System with Dilation Feature," filed Dec. 4, 2012, published as U.S. Pat. Pub. No. 2014/0151429 on Jun. 5, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,951, entitled "Surgical Staple with Integral Pledget for Tip Deflection," filed Nov. 29, 2012, published as U.S. Pat. Pub. No. 2014/0144968 on May 29, 2014, now U.S. Pat. No. 9,289,207, issued Mar. 22, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/706,827, entitled "Surgical Stapler with Varying Staple Widths Along Different Circumferences," filed Dec. 6, 2012, published as U.S. Pat. Pub. No. 2014/0158747 on Jun. 12, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,992, entitled "Pivoting Anvil for Surgical Circular Stapler," filed Nov. 29, 2012, published as U.S. Pat. Pub. No. 2014/0144969 on May 29, 2014, now U.S. Pat. No. 9,498,222, issued Oct. 11, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/693,455, entitled "Circular Anvil Introduction System with Alignment Feature," filed Dec. 4, 2012, published as U.S. Pat. Pub. No. 2014/0151430 on Jun. 5, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,308, entitled "Circular Stapler with Selectable Motorized and Manual Control," filed on even date herewith, published as U.S. Pat. Pub. No. 2014/0166727 on Jun. 19, 2014, now U.S. Pat. No. 9,445,816, issued Sep. 20, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,313, entitled "Circular Stapler with Selectable Motorized and Manual Control, Including a Control Ring," filed on even date herewith, published as U.S. Pat. Pub. No. 2014/0166767 on Jun. 19, 2014, now U.S. Pat. No. 9,532,783, issued Jan. 3, 2017, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,323, entitled "Motor Driven Rotary Input Circular Stapler with Lockable Flexible Shaft," filed on even date herewith, published as U.S. Pat. Pub. No. 2014/0166718 on Jun. 19, 2014, now U.S. Pat. No. 9,463,022, issued Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for stapling tissue, the apparatus comprising:
   (a) a body assembly;
   (b) a rotary drive shaft, wherein the rotary drive shaft is translatable between a first longitudinal position and a second longitudinal position relative to the body assembly; and
   (c) a stapling assembly, wherein the stapling assembly comprises:
      (i) an anvil,
      (ii) a staple deck,
      (iii) a staple driver operable to drive staples through the staple deck and toward the anvil,
      (iv) a first drive member operable to move the anvil toward the staple deck in response to rotation of the drive shaft in the first longitudinal position, and
      (v) a second drive member operable to move the staple driver toward the anvil in response to rotation of the drive shaft in the second longitudinal position.

2. The apparatus of claim 1, wherein the anvil includes an annular array of staple forming pockets.

3. The apparatus of claim 1, wherein the body assembly includes a drive shaft translation input operable to translate the drive shaft between the first longitudinal position and the second longitudinal position.

4. The apparatus of claim 1, wherein the body assembly includes a motor operable to rotate the drive shaft.

5. The apparatus of claim 1, wherein the stapling assembly further includes a blade feature operable to cut tissue.

6. The apparatus of claim 5, wherein the second drive member is further operable to move the blade feature toward the anvil in response to rotation of the drive shaft in the second longitudinal position.

7. The apparatus of claim 1, wherein the stapling assembly further comprises a trocar coupled with the anvil.

8. The apparatus of claim 7, wherein the trocar is threadably coupled with the first drive member.

9. The apparatus of claim 1, wherein the drive shaft has a distally presented recess, wherein the first drive member includes a proximal drive feature, wherein the recess of the drive shaft is configured to receive the drive feature of the first drive member in response to the drive shaft being in the first longitudinal position, wherein the drive shaft is configured to decouple the drive feature of the first drive member in response to the drive shaft being in the second longitudinal position.

10. The apparatus of claim 1, wherein the drive shaft has a set of distal splines, wherein the second drive member has a set of proximal splines, wherein the distal splines of the drive shaft are configured to mesh with the proximal splines of the second drive member in response to the drive shaft being in the second longitudinal position; wherein the drive shaft is configured to decouple the distal splines of the drive shaft from the proximal splines of the second drive member in response to the drive shaft being in the first longitudinal position.

11. The apparatus of claim 1, wherein the second drive member comprises a rotatable member and a translating member threadably coupled with the rotatable member, wherein the translating member is operable to linearly drive the staple driver.

12. The apparatus of claim 1, further comprising a shaft assembly extending distally from the body, wherein the shaft assembly defines a distal socket, wherein the drive shaft has a distal end located within the distal socket.

13. The apparatus of claim 12, wherein the stapling assembly further comprises a cartridge body, wherein the cartridge body houses the staple deck, the staple driver, the first drive member, and the second drive member, wherein at least part of the cartridge body is inserted in the distal socket of the shaft assembly.

14. The apparatus of claim 13, wherein the cartridge body includes a pair of resiliently biased tabs, wherein the pair of resiliently biased tabs is operable to removably secure the cartridge body within the distal socket of the shaft assembly.

15. The apparatus of claim 14, wherein the distal socket includes a pair of apertures, wherein each of the apertures is configured to receive one of the resiliently biased tabs.

16. A staple cartridge, comprising:
   (a) a cartridge body, wherein the cartridge body is substantially cylindraceous, wherein the cartridge body is configured to removably couple with a stapling instrument;
   (b) a staple deck, wherein the staple deck includes an annular array of openings;
   (c) a staple driver, wherein the staple driver is operable to drive staples through the annular array of openings; and
   (d) a first rotary drive member in communication with the staple driver, wherein the first rotary drive member is rotatable relative to the cartridge body to drive the staple driver, to thereby drive staples through the annular array of openings;
   (e) a trocar, wherein the trocar is operable to couple with an anvil; and
   (f) a second rotary drive member, wherein the second rotary drive member is rotatable relative to the cartridge body to retract the trocar relative to the staple deck; wherein the first rotary drive member and the second rotary drive member are rotatable independently relative to each other.

17. The staple cartridge of claim 16, wherein the first rotary drive member and the second rotary drive member are coaxially aligned with each other.

18. An apparatus for stapling tissue, the apparatus comprising:
   (a) a handle assembly;
   (b) a shaft assembly extending distally from the handle assembly, the shaft assembly including a rotary drive shaft; and
   (c) a stapling head assembly secured to the distal end of the shaft assembly, wherein the stapling head assembly comprises:
      (i) a first actuator operable to clamp tissue against the stapling head assembly in response to rotation of the rotary drive shaft, and
      (ii) a second actuator operable to staple tissue adjacent to the stapling head assembly in response to rotation of the rotary drive shaft,
      wherein the rotary drive shaft is operable to translate between engagement with the first actuator and engagement with the second actuator.

* * * * *